United States Patent
Villefrance et al.

(10) Patent No.: US 9,629,744 B2
(45) Date of Patent: *Apr. 25, 2017

(54) DRAINABLE OSTOMY POUCH WITH INTEGRATED CLOSURE

(75) Inventors: Tine Villefrance, Herlev (DK); Jørgen Forbjerg-Larsen, Skaevinge (DK); Knud Winther, Snekkersten (DK)

(73) Assignee: Hollister Incorporated, Libertyville, IL (US)

( * ) Notice: Subject to any disclaimer, the term of this patent is extended or adjusted under 35 U.S.C. 154(b) by 992 days.

This patent is subject to a terminal disclaimer.

(21) Appl. No.: 12/973,073

(22) Filed: Dec. 20, 2010

(65) Prior Publication Data

US 2011/0144601 A1 Jun. 16, 2011

Related U.S. Application Data

(63) Continuation of application No. 10/510,365, filed as application No. PCT/DK03/00223 on Apr. 7, 2003, now Pat. No. 7,879,015.

(30) Foreign Application Priority Data

Apr. 10, 2002 (DK) .................................. 2002 00529

(51) Int. Cl.
*A61F 5/44* (2006.01)
*A61F 5/445* (2006.01)
(Continued)

(52) U.S. Cl.
CPC ............ *A61F 5/445* (2013.01); *A61F 5/4405* (2013.01); *A61F 5/4407* (2013.01); *B65D 33/02* (2013.01); *B65D 33/24* (2013.01)

(58) Field of Classification Search
CPC ...... A61F 5/445; A61F 5/4405; A61F 5/4407; B65D 33/02; B65D 33/24
(Continued)

(56) References Cited

U.S. PATENT DOCUMENTS 2,520,831 A    8/1950  Chincholl
2,782,785 A    2/1957  Arcand
(Continued)

FOREIGN PATENT DOCUMENTS

DE    29 36 622 A1    3/1981
FR    2 870 112 A1    11/2005
(Continued)

OTHER PUBLICATIONS

Opposition against corresponding European Patent No. EP 1496820, dated May 7, 2009.
(Continued)

*Primary Examiner* — Tatyana Zalukaeva
*Assistant Examiner* — Andrew J Mensh
(74) *Attorney, Agent, or Firm* — Levenfeld Pearlstein, LLC

(57) ABSTRACT

A drainable ostomy pouch is disclosed which comprises a first or proximal and a second or distal side wall of flexible sheet material sealed to each other for defining a cavity therebetween for receiving human stomal discharge through an aperture in the proximal side wall. It includes an elongate drainage portion extending downwardly in a longitudinal direction and ending in a drainage opening extending transversely to the longitudinal direction, and a first or proximal and a second or distal flexible stiffening strip of relatively stiff material extending immediately adjacent to and along the drainage opening and being attached to the outer surface of the first and second side walls, respectively, of the drainage portion. The pouch further comprises a securing strip having interlocking elements on the wall and corresponding interlocking elements on a flap for securing a coil comprising the first and second stiffening strips rotated upwards at least two times.

10 Claims, 3 Drawing Sheets

(51) Int. Cl.
*B65D 33/24* (2006.01)
*B65D 33/02* (2006.01)

(58) Field of Classification Search
USPC .................................................. 604/332, 340
See application file for complete search history.

(56) References Cited

U.S. PATENT DOCUMENTS

| | | | |
|---|---|---|---|
| 3,189,253 A | 6/1965 | Mojonnier | |
| 3,251,390 A | 5/1966 | Evans | |
| 3,406,853 A | 10/1968 | McLeod | |
| 3,408,705 A | 11/1968 | Kayser et al. | |
| 3,473,532 A | 10/1969 | Eisenberg | |
| 3,507,282 A | 4/1970 | Burding | |
| 3,523,534 A * | 8/1970 | Nolan | 604/335 |
| 3,567,074 A | 3/1971 | Brown | |
| 3,688,973 A | 9/1972 | Lillkvist | |
| 3,690,320 A | 9/1972 | Riely | |
| 3,724,461 A | 4/1973 | Eisenberg | |
| 3,734,154 A | 5/1973 | Polk | |
| 3,825,005 A | 7/1974 | Fenton | |
| 3,897,780 A | 8/1975 | Trousil | |
| 3,924,631 A | 12/1975 | Mancusi, Jr. | |
| 4,050,468 A | 9/1977 | Wynnyk | |
| 4,230,115 A | 10/1980 | Walz, Jr. et al. | |
| 4,233,977 A | 11/1980 | Mattson | |
| 4,310,952 A | 1/1982 | Robben et al. | |
| 4,411,659 A | 10/1983 | Jensen et al. | |
| 4,439,191 A | 3/1984 | Hogan | |
| 4,441,659 A | 4/1984 | Marklund | |
| 4,460,359 A | 7/1984 | Fenton | |
| 4,465,486 A | 8/1984 | Hill | |
| 4,561,540 A | 12/1985 | Hunter et al. | |
| 4,596,566 A | 6/1986 | Kay | |
| 4,686,814 A | 8/1987 | Yanase et al. | |
| 4,755,177 A | 7/1988 | Hill | |
| 4,838,874 A | 6/1989 | Eisenberg | |
| 4,869,725 A | 9/1989 | Schneider et al. | |
| 4,898,477 A | 2/1990 | Cox et al. | |
| 4,983,172 A | 1/1991 | Steer et al. | |
| 4,988,343 A | 1/1991 | Ballan et al. | |
| 5,000,500 A | 3/1991 | Almog et al. | |
| 5,030,211 A | 7/1991 | Zakroczymski | |
| 5,037,138 A | 8/1991 | McClintock et al. | |
| 5,037,149 A | 8/1991 | Beck | |
| 5,044,774 A | 9/1991 | Bullard et al. | |
| 5,174,658 A | 12/1992 | Cook et al. | |
| 5,184,896 A | 2/1993 | Hammond et al. | |
| 5,457,855 A | 10/1995 | Kenney et al. | |
| 5,545,154 A | 8/1996 | Oberholtzer | |
| D379,654 S | 6/1997 | Holtermann | |
| 5,643,234 A | 7/1997 | Lesko | |
| 5,647,670 A | 7/1997 | Iscovich | |
| 5,690,621 A | 11/1997 | Canela | |
| 5,690,623 A * | 11/1997 | Lenz et al. | 604/333 |
| 5,745,926 A | 5/1998 | Cailleteau | |
| 5,941,640 A | 8/1999 | Thatcher | |
| 5,968,023 A | 10/1999 | Olsen | |
| 5,968,024 A | 10/1999 | Freeman | |
| 6,212,716 B1 | 4/2001 | Logan, Jr. et al. | |
| 6,267,506 B1 | 7/2001 | Campion | |
| 6,336,918 B1 | 1/2002 | Olsen et al. | |
| 6,419,664 B1 | 7/2002 | von Bulow et al. | |
| 6,544,241 B2 | 4/2003 | Morton | |
| 6,589,221 B1 | 7/2003 | Olsen et al. | |
| 6,726,667 B2 * | 4/2004 | Leise et al. | 604/339 |
| 6,764,473 B2 * | 7/2004 | Morton | 604/334 |
| 6,858,023 B2 | 2/2005 | Poulsen | |
| 6,887,222 B2 | 5/2005 | Mandzij et al. | |
| 7,306,581 B2 | 12/2007 | Falconer et al. | |
| 7,879,015 B2 * | 2/2011 | Villefrance et al. | 604/332 |
| 7,879,016 B2 * | 2/2011 | Mandzij et al. | 604/335 |
| 7,947,025 B2 * | 5/2011 | Buglino et al. | 604/335 |
| 2001/0037627 A1 | 11/2001 | Hausslein | |
| 2002/0010444 A1 | 1/2002 | Wiltshire et al. | |
| 2002/0111659 A1 | 8/2002 | Davis et al. | |
| 2002/0165507 A1 | 11/2002 | Hessel et al. | |
| 2003/0028160 A1 | 2/2003 | Leise et al. | |
| 2003/0073962 A1 | 4/2003 | Olsen et al. | |
| 2003/0167042 A1 | 9/2003 | Poulsen | |
| 2005/0131360 A1 | 6/2005 | Villefrance et al. | |
| 2007/0265588 A1 | 11/2007 | Pedersen | |
| 2009/0043271 A1 | 2/2009 | Winther | |

FOREIGN PATENT DOCUMENTS

| | | |
|---|---|---|
| GB | 2 000 683 A | 1/1979 |
| GB | 2 268 065 A | 1/1994 |
| GB | 2 346 328 A | 8/2000 |
| GB | 2 398 743 A | 9/2004 |
| GB | 2 414 677 A | 12/2005 |
| WO | WO-96/19164 A1 | 6/1996 |
| WO | WO-99/25278 A1 | 5/1999 |
| WO | WO-01/28470 A1 | 4/2001 |
| WO | WO-01/51383 A1 | 7/2001 |
| WO | WO-03/065944 A1 | 8/2003 |

OTHER PUBLICATIONS

International Search Report tor Application No. PCT/DK03/00223, dated Jul. 1, 2003.

* cited by examiner

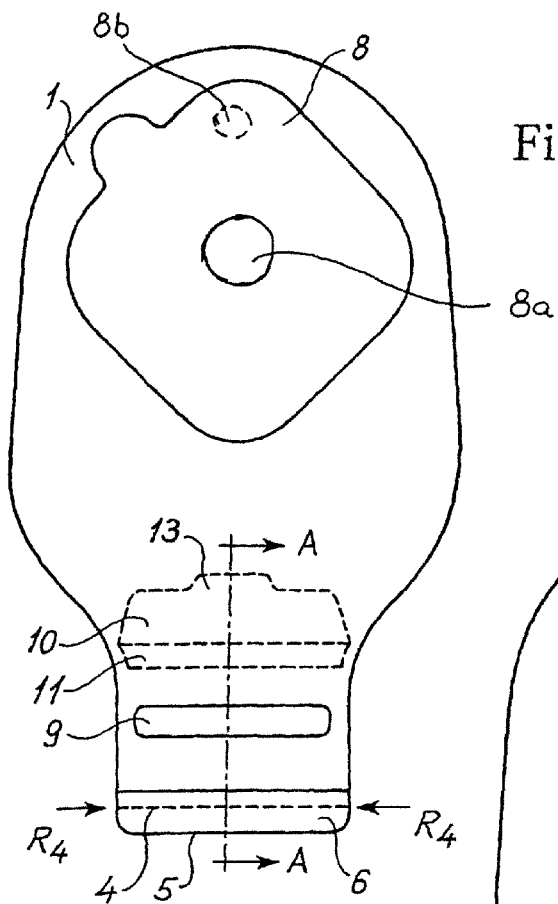
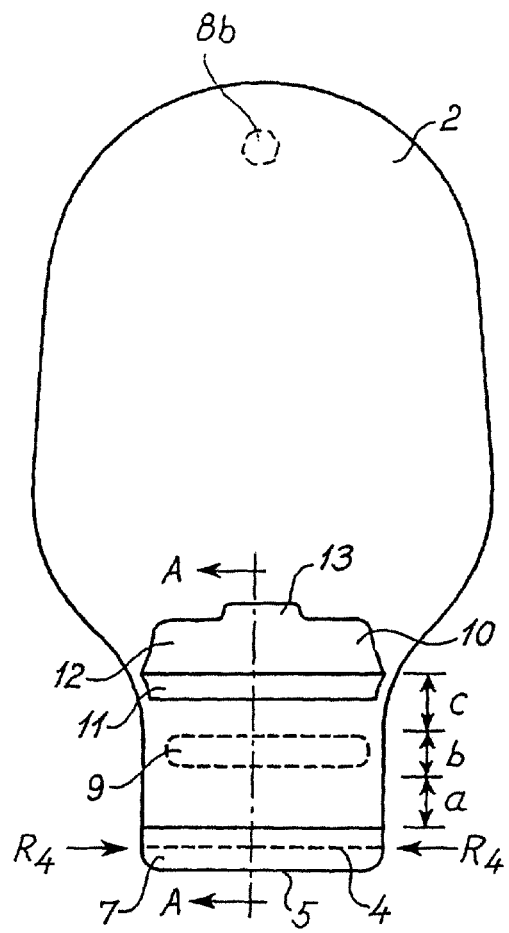
Fig. 1
Fig. 2

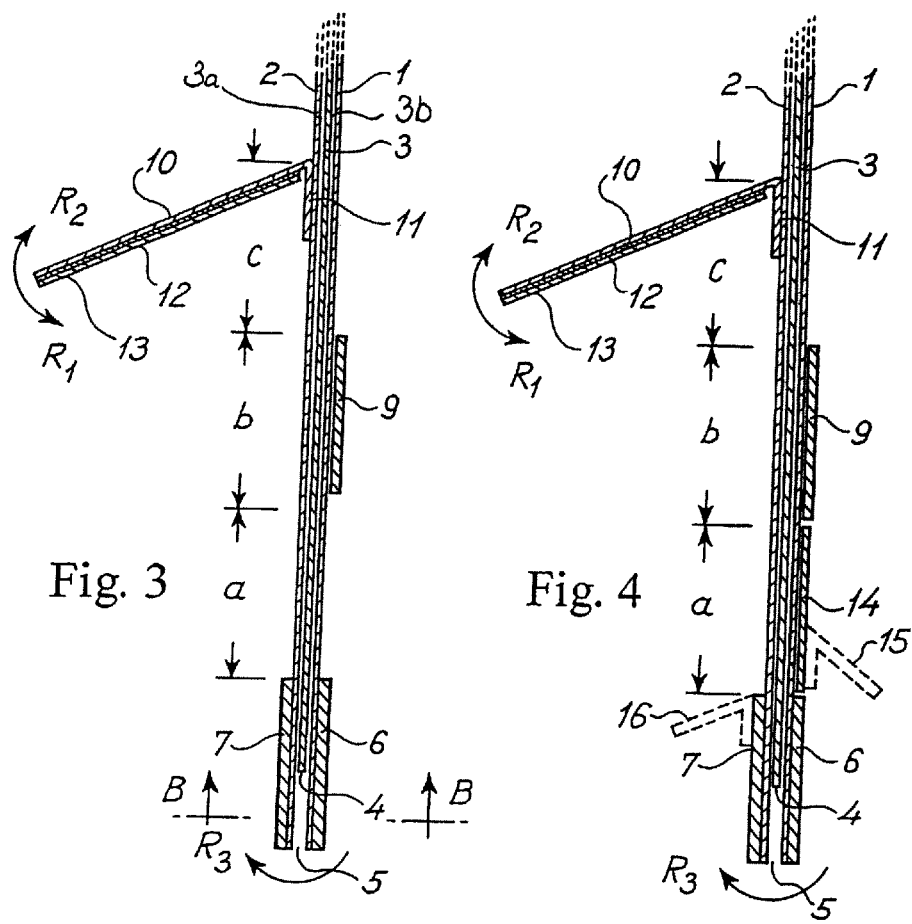
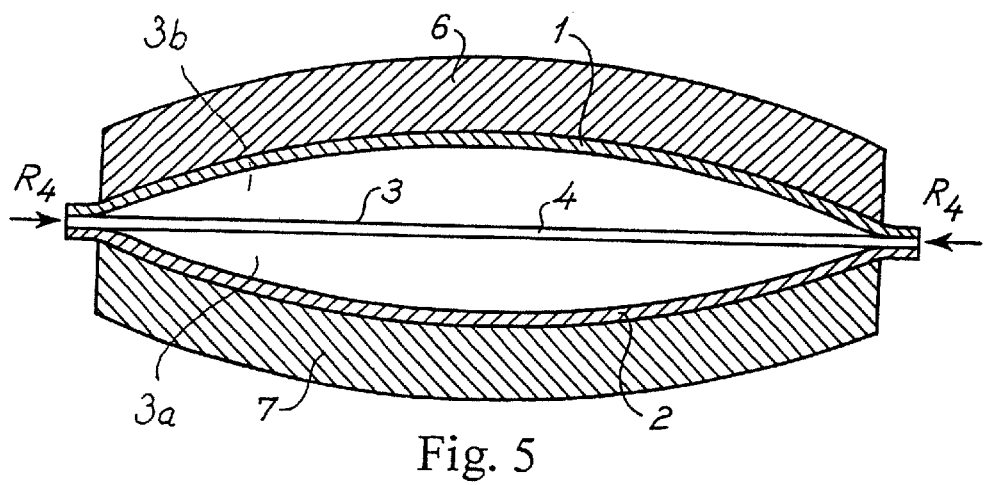

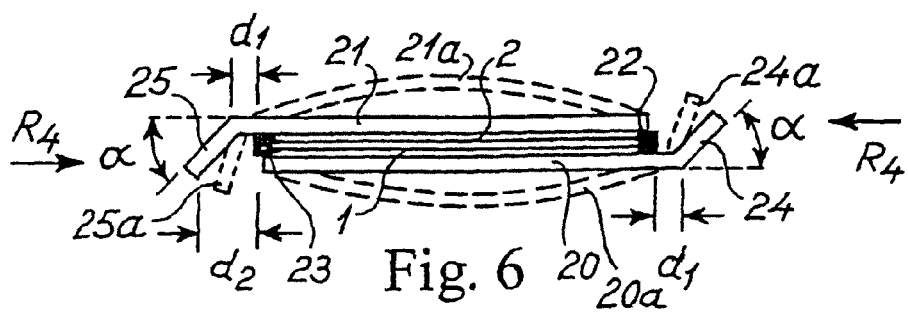
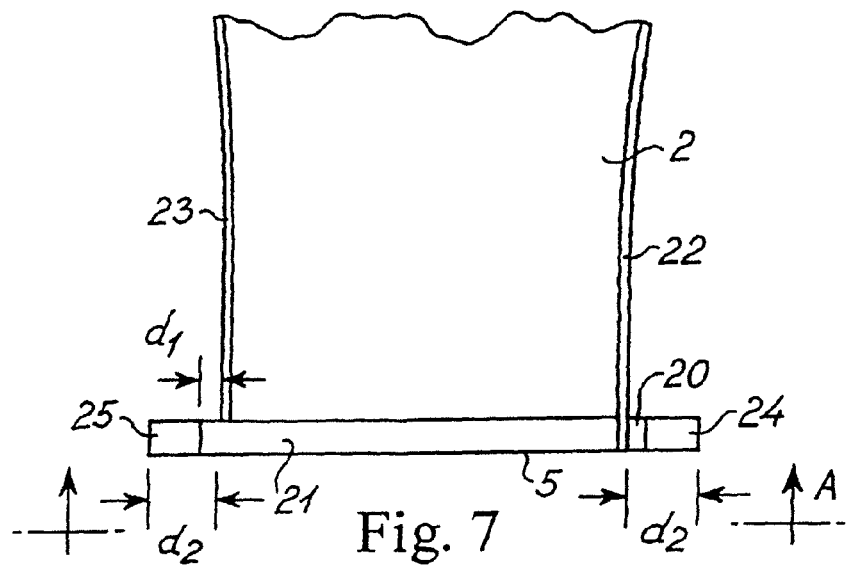
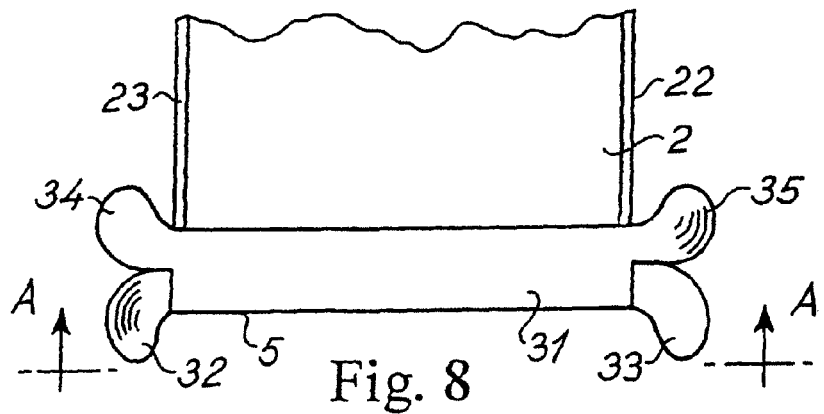
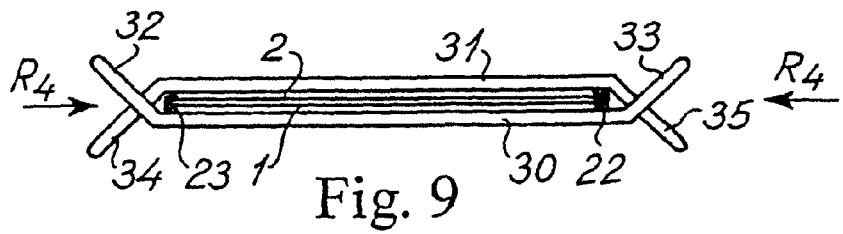

DRAINABLE OSTOMY POUCH WITH INTEGRATED CLOSURE

REFERENCE TO RELATED APPLICATIONS

This disclosure claims priority, as a Continuation under 35 USC §120, to co-pending application Ser. No. 10/510,365, filed Feb. 7, 2005, now U.S. Pat. No. 7,879,015 which claims the benefit of the filing date, and is the national stage of International Application No. PCT/DK03/00223, having an international filing date of Apr. 7, 2003, which designated the United States of America, and which also claims priority to Denmark Patent Application No. PA-200200529, filed Apr. 10, 2002.

BACKGROUND

Field of the Disclosure

The present invention relates to a drainable ostomy pouch comprising a first or proximal and a second or distal side wall of flexible sheet material sealed to each other for defining a cavity therebetween for receiving human stomal discharge through an aperture in said proximal side wall and an elongate drainage portion extending downwardly in a longitudinal direction thereof and ending in a drainage opening extending transversely to said longitudinal direction.

Description of the Existing Art

In connection with the use of such ostomy pouches, several considerations are of great importance to the quality of life of the persons utilizing the pouches. The pouches should be easy to drain without risking soiling of clothes or the surroundings, they should be easy to close securely after being drained and they should be amenable to being cleaned after drainage and before closing again such that the risk of unpleasant odours is substantially reduced.

Many different solutions concerning the closing, cleaning and drainage operations have been proposed and implemented. These solutions all have serious disadvantages regarding security of the closure, requirements to dexterity often not at hand for elderly persons, difficult cleaning procedures, and so on.

UK patent application No. GB 2 000 683 discloses a drainable ostomy pouch of the type in reference having a bar of relatively rigid polymeric material bonded to the outer surface of the distal side wall at the bottom of the drainage portion adjacent and along a drainage aperture extending transversely to the longitudinal direction of the drainage portion. This bar is utilized to facilitate folding of the drainage portion in said longitudinal direction until a transversely extending strip of Velcro® attached to the proximal side wall can be engaged by a corresponding strip of Velcro® located on a transversely extending flap attached to said distal wall.

The drainage aperture and the area surrounding it are difficult to clean because of the thin proximal wall film not being easy to locate and separate from the bar for cleaning and removing any elongate material between said film and the bar. Furthermore, when folding the drainage portion upwards the end of the proximal wall film may be displaced upwards and wrinkled thereby increasing the risk of a deficient closure with leakage occurring along said wrinkles.

SUMMARY

One of the objects of the present invention is to provide a drainable ostomy pouch where the cleaning of the drainage aperture and the region surrounding it is facilitated and where the folding procedure is such that a secure and tight coil is formed with no risk of formation of a leakage passage along wrinkles of the proximal wall film.

According to the invention, this object is achieved by the pouch comprising a first or proximal and a second or distal flexible stiffening strip of relatively stiff material such as PET, nylon, high density polyethylene, low density polyethylene or polypropylene extending immediately adjacent to and along said drainage opening and being attached for instance by heat sealing or adhesion to the outer surface of said first and second side walls, respectively, of said drainage portion, the pouch further comprising securing means for securing in coiled condition a coil comprising said first and second stiffening strips as well as the corresponding area of the first and second side walls of said drainage portion rotated upwards at least two times, preferably three times.

Hereby, the cleaning may be performed easily and efficiently by pressing the two stiffening strips against one another to press out any material therebetween such that it can be cleaned away by wiping the superimposed edges of the strips adjacent the drainage aperture for instance with a tissue. Any elongate material between the strips that cannot be pressed out may be removed by separating the strips that are relatively easy to separate compared to separating a thin film from a strip. During the folding process there is no danger of wrinkles forming in the proximal film near the drainage aperture because it is held flat by the attached stiffening strip.

In the currently preferred embodiment of an ostomy pouch according to the invention, said securing means comprise a securing strip of sheet material having a first and a second securing strip surface and a first and a second securing strip longitudinal edge, said securing strip being attached to the outer surface of said first pouch side wall in a substantially parallel relationship with said drainage opening by means of an attachment zone of said first securing strip surface extending along and adjacent said first securing strip longitudinal edge, an area of said securing strip second surface being covered by a first part of an interlocking means for cooperating with a second part of a corresponding interlocking means provided on the outer surface of said second pouch wall.

Hereby, said attachment zone will lie under the coil when the coil is locked beneath the flap thereby affording a more stable securing of the coil under the flap. Furthermore because of the resulting fold between the attachment zone and the rest of the flap, the flap will tend to project outwards when the coil is being formed by rotating the stiffening strips and therefore it is easy to grip the flap to lock the coil.

In the currently preferred embodiment, a gripping tab for being gripped by fingers of a hand projects from said second securing strip longitudinal edge. This facilitates the disengagement of the two interlocking means when the drainage portion is to be unfolded for emptying the pouch.

Preferably, the edge of said attachment zone remote from said first securing strip longitudinal edge is spaced from said drainage opening by a distance substantially equal to a multiple, preferably three, of the width of the widest of said first and second stiffening strips. Hereby the coil will fit snugly and tightly adjacent the fold separating the attachment zone and the rest of the flap thereby affording a more stable securing of the coil under the flap.

Advantageously, the ostomy pouch may further be provided with a third intermediate wall of flexible sheet material arranged between said first and second side walls for dividing said cavity into two compartments and ending at a transversely extending bottom edge located between said first and second stiffening strips and spaced from said drainage opening, preferably by approximately half the width of the narrowest of said first and second stiffening strips.

By arranging said bottom edge at a distance from the bottom of the drainage portion, the bottom edge will not interfere with the cleaning process, but by leaving said bottom edge between the stiffening strips it is avoided that a leakage may develop between said two compartments because of displacement and/or wrinkling of the intermediate wall.

Preferably, said intermediate wall is provided at or near its upper end with an opening for the passage of flatus gasses between said compartments.

Advantageously, the two side walls of the drainage portion may be attached to each other along the longitudinal edges thereof by means of edge seams of heat sealing or adhesive, and at least one of said stiffening strips may extend beyond one of said edge seams. Hereby it is obtained that the stiffening strips will flex away from one another for controlling the drainage rate and for cleaning purposes if pressure is applied to the ends thereof in the longitudinal direction of the strips because of a flexing torque developed with said one of said seams as a fulcrum.

Said proximal stiffening strip may by configured such that at least one of the two opposed end portions thereof slopes in the distal direction and/or said distal stiffening strip may be configured such that at least one of the two opposed end portions thereof slopes in the proximal direction thereof. Flexing torques for flexing the stiffening strips away from one another will develop when pressure is applied to the end portions of the sloped portions in the longitudinal direction of the strips.

The entire length of said sloped end portion may extend beyond the corresponding edge seam of the drainage portion, and said sloped portion may be substantially rectilinear in the longitudinal direction of the corresponding stiffening strip, or said sloped portion may be arcuate in the longitudinal direction of the corresponding stiffening strip.

Preferably, said proximal stiffening strip is provided with a single one of said sloped end portions or extensions located at one end of said drainage opening and said distal stiffening strip is provided with a single one of said sloped end portions or extensions located at the opposite end of said drainage opening. Hereby a substantially symmetrical flexing of the stiffening strips away from one another is obtained when said longitudinal pressure is applied.

Advantageously, at least one of said stiffening strips may be curved in the longitudinal direction thereof such that the surface of said stiffening strip attached to the corresponding side wall is concave in the longitudinal direction of said stiffening strip. Hereby an inherent tendency of the stiffening strips to flex away from one another under said pressure applied longitudinally to the ends thereof is built into the strips.

Advantageously, a gripping tab of flexible sheet material may be attached to the outer surface of the distal and/or proximal side wall or stiffening strip in the region near said drainage opening. Hereby a very effective means is provided for separating the stiffening strips for cleaning and flexing purposes.

In the following, the invention will be explained more in detail in connection with various embodiments thereof shown, solely be way of example, in the accompanying drawings, where:

BRIEF DESCRIPTION OF THE SEVERAL VIEWS OF THE DRAWING

FIGS. 1 and 2 are schematic plan views of the proximal and distal sides, respectively, of a currently preferred embodiment of a pouch according to the invention, FIG. 3 is a schematic enlarged scale cross-sectional view of the elongate drainage portion of the pouch of FIGS. 1-2 taken along line A-A in FIGS. 1 and 2, FIG. 4 is a view similar to FIG. 3 of a second embodiment of a pouch according to the invention, FIG. 5 is a schematic enlarged scale cross-sectional view taken along line B-B in FIG. 3, FIGS. 6 and 7 are a schematic end view and plan view, respectively, of a third embodiment of a pouch according to the invention, the end view in FIG. 6 being taken along line A-A in FIG. 7, and FIGS. 8 and 9 are a schematic plan view and end view, respectively, of a fourth embodiment of a pouch according to the invention, the end view in FIG. 9 being taken along line A-A in FIG. 8.

DETAILED DESCRIPTION OF THE PREFERRED EMBODIMENTS

The ostomy pouch according to the invention may be part of a one-piece or of a two-piece ostomy appliance.

Referring now to FIGS. 1-3, the currently preferred embodiment of an ostomy pouch according to the invention comprises three sheets or films of a liquid and gas impermeable flexible material, a body side or proximal film 1, an opposed or distal film 2 and an intermediate film 3 having a bottom edge 4 and dividing the pouch into a flatus gas chamber 3*a* and a faeces chamber 3*b*.

An elongate drainage portion ending in a drainage opening or outlet 5 defined by the lower ends of films 1 and 2 extends downwards from the main portion of the pouch.

A proximal stiffening strip 6 and a distal stiffening strip 7 of a relatively stiff, flexible plastic material such as PET, nylon, HDPE or LDPE are attached to the outer surfaces of the lower ends of the films 1 and 2, respectively, and extend immediately adjacent and along the entire length of the drainage opening 5.

The distance of the bottom edge 4 of the intermediate film 3 from the discharge aperture 5 is approximately half the width of strips 6 and 7. A face plate 8 of a skin friendly adhesive barrier material is attached to film 1. The face plate 8 serves to attach the pouch to the peristomal skin surface of a wearer of the ostomy pouch in a manner well known in the art.

The face plate 8 and the film 1 to which the face plate is attached are provided with aligned stoma-receiving apertures 8*a* or, alternatively, with aligned starter openings which may be enlarged at the time of application by cutting with scissors, all as well known in the art. Also, intermediate film 3 is provided at or near it uppers limits with an opening 8*b* for allowing flatus gasses to pass from the faeces chamber 3*b* to the flatus gas chamber 3*a* while at same time preventing or restraining the passage of faecal material from chamber 3*b* to chamber 3*a*, as shown and described in U.S. Pat. No. 5,690,623, the disclosure of which is incorporated by reference herein.

A strip 9 of an interlocking means such as Velcro® (hook or loop portion), DUOTEC™ from G. Binder GmbH & Co., Germany (interlocking mushroom elements) or well known repeatedly releasable adhesive coatings, is attached to film 1.

A flap 10 of flexible film material is attached to film 1 by welding or glueing an edge portion 11 of flap 10 to film 2. A strip 12 of a corresponding interlocking means such as Velcro® (loop or hook portion), DUOTEC™ or said repeatedly releasable adhesive coating is attached to the flap 10.

The flap 10 is shown in different positions in FIGS. 1, 2 and in FIG. 3, the position of flap 10 shown in FIG. 3 being rotated in the direction R1 compared to the position of flap 10 shown in FIGS. 2 and 3 where the flap 10 abuts the film 2, i.e. being rotated as far as possible in the direction R2. The flap 10 has a gripping tab 13 for being gripped by the user's fingers.

In use, the discharge portion of the pouch is closed in the following manner after having been emptied through the drainage aperture 5:

The strips 6 and 7 are pressed together to squeeze any remaining matter out from the area between the strips 6 and 7. If any material between the strips 6 and 7 cannot be pressed out, the strips are pulled or flexed apart so as to be able to access said material for removal. The edges of the strips 6 and 7 constituting the discharge aperture 5 are then wiped clean with a tissue.

Thereafter the strips 6 and 7 are rotated clock-wise in the direction of arrow R3 until strip 7 abuts the area a of film 2. Thereafter the strips 6 and 7 are rotated 15 once more clock-wise until strip 6 abuts area b of film 2.

Finally, the strips 6 and 7 are rotated one last time clock-wise such that the coil formed by the strips 6, 7 and 9 as well as the portions of films 1, 2 and 3 involved abuts the area c of film 2 with the strip 9 of Velcro® or the like located such that the corresponding strip 12 of Velcro® or the like can engage it by rotating the flap 10 in the direction R1 until the two Velcro® strips 9 and 12 abut and engage each other for locking said coil in the final closed and secured position of the discharge portion.

In this closed coiled position the upper edge of the coil should preferably fit snugly and tightly in the angle formed between the portion 11 and the rest of the flap 10 such that pressure is exerted thereby on the coil and the portion 11 which is beneficial to the stability of the closure. The rigidity of the strips 6 and 7 is also important for the stability of the closure.

The angle or fold between the portion 11 and the rest of the flap 10 furthermore affords the advantage that the flap 10 in its relaxed state will tend to be in an open position not abutting film 2 in which it is easy to grip when rolling the discharge portion up.

When the pouch is to be drained, the flap 10 is gripped by the tab 13 and pulled such that the strips 9 and 12 are disengaged so that the coil can be unrolled by rotating the strips 6 and 7 three times in the counter clock-wise direction.

The strips 6 and 7 may be used to control the rate of drainage of the pouch by opening and closing the aperture 5 by pressing more or less forcefully on the ends of the strips 6 and 7 in the direction of the arrows R4 so that they flex away from and towards each other, respectively.

This function is facilitated by configuring the strips 6 and 7 in the manner shown exaggerated in FIG. 5 of the drawings which shows a longitudinal cross section through the strips 6 and 7 in relaxed state illustrating that the strips are manufactured with opposed curvatures which will tend to facilitate the opening of the aperture 5 by finger pressure in the directions R4.

To facilitate a tight and precise coiling or folding of the drainage portion, the drainage portion may be configured as shown in FIG. 4, where a further strip 14 of relatively rigid and flexible plastic material is adhered to and nearly covers the area a of film 1 while the Velcro® strip 9 is wider than in FIG. 3 so that it nearly covers the area b of film 1. Hereby a precise and tight folding of the discharge portion is facilitated so that the best possible closure under the flap 10 is ensured. The thickness of strip 14 may be smaller than the thickness of strips 6 and 7.

So as to further facilitate precise and tight coiling of the discharge portion, a further strip may be adhered to film 1 nearly covering region c thereof.

The distance between the bottom edge 4 of intermediate film 3 and the discharge aperture 5 has the advantage that it thereby is easier to separate the three films for cleaning purposes.

Furthermore, by locating the edge 4 between the strips 6 and 7 it is ensured that film 3 is held flat without wrinkles and folded just as many times as the films 1 and 2 such that there is no risk of leaks below the intermediate film 3 between the flatus gas chamber 3*a* and the faeces chamber 3*b* in the rolled-up closed position of the drainage portion.

Referring now to FIG. 4, two gripping tabs 15 and 16 are shown with dotted lines, the tab 15 being adhered or heat sealed to film 1 and tab 16 being adhered or heat sealed to strip 7. It is sometimes difficult to separate the strips 6 and 7 for opening the aperture 5 for draining the pouch because of a suction effect between the strips analogous to the adherence of two superimposed glass plates to one another, particularly if the drainage aperture region is moist. In such case tabs 15 and 16 can be used for pulling the strips 6 and 7 apart. The tabs 15 and 16 may both be attached to the strips 6 and 7, respectively, or to films 1 and 2, respectively.

Referring now to FIGS. 6 and 7, a proximal strip 20 and a distal strip 21 similar to strips 6 and 7 in FIGS. 1-4 are adhered to the films 1 and 2, respectively. One end of each strip 20 and 21 extends beyond longitudinal edge seams 22 and 23, respectively, of the drainage portion with a projecting end portion 24 and 25, respectively, that is angled an angle a in the distal and proximal direction, respectively.

The ends of strips 20 and 21 opposite the end portions 24 and 25, respectively are located on or immediately adjacent the lateral edge seams 22 and 23, respectively. The start of the angled portions 24 and 25 are located a distance d1 from said seams 22 and 23, respectively, and the ends of angled portions 24 and 25 are located at a distance d2 from said seams 22 and 23, respectively.

When pressure is applied by fingers to the ends of end portions 24 and 25 in the directions R4, said portions will be deflected to the positions 24*a* and 25*a* shown by dotted lines in FIG. 6 and the resultant torque around the fulcrums or pivoting points constituted by the edge seams 22 and 23, respectively, will cause the strips 20 and 21 to flex apart into the positions 20*a* and 21*a*, respectively, indicated by dotted lines in FIG. 6.

The distance d1 mentioned above allows the end portions 24 and 25 to flex without being hindered by abutting the ends of strips 21 and 20, respectively.

The larger the distance d2 is, the larger is the torque applied to the strips 20 and 21 for a given pressure exerted on said ends of the end portions in the 10 directions R4.

Experiments have shown that the angle a may be very small and even equal to zero because when applying said pressure in the directions R4 the longitudinal displacement of the strips 20 and 21 relative to each other and the resulting deformation of the edge seams 22 and 23 will bias the end portions 24 and 25 to flex in the desired direction even with a value of a equal to zero. Even with small negative values of a, a flexing torque in the correct direction may be obtained by said pressure depending on the actual geometric configuration of the seams relative to the strips. A certain angling with a positive value of a will, however, ensure that flexing torques in the correct direction will be achieved even with relatively large production tolerances.

The angled end portions 24 and 25 are shown to be rectilinear, but they may be curved as long as a tendency to flex in the desired direction under said pressure is maintained so as to generate the required torques for flexing the strips 20 and 21.

The edge seams 22 and 23 and thereby the edges of the drainage portion are shown extending substantially parallel to one another such that the end portions 24 and 25 will not interfere with the rolling up closure operation. The edge seams may taper slightly towards one another from the strips 24 and 25 in the upwards direction so as to further ensure no such interference.

Referring now to FIGS. 8 and 9, stiffening strips 30 and 31 similar to stiffening strips 20 and 21 in FIGS. 6 and 7 have extended angled and rounded end portions 32,33 and 34,35, respectively. Pressure exerted by fingers on the rounded ends in the directions R4 will produce torques around edge seams 22 and 23 and flex strips 30 and 31 away from each other in a manner similar to the situation for strips 20a and 21a indicated in FIG. 6 by dotted lines.

We claim:

1. A drainable ostomy pouch comprising a proximal and a distal side wall each including a liquid and gas impermeable film, said films being sealed to each other for defining: i) a cavity formed of said films for receiving human stomal discharge through an aperture in said proximal side wall and ii) an elongate drainage portion formed of said films in communication with said cavity and extending downwardly from said cavity in a longitudinal direction thereof, said elongate drainage portion ending in a drainage opening defined by lower ends of said films extending transversely to said longitudinal direction, a proximal and a distal flexible stiffening strip of relatively stiff material on said elongate drainage portion and being attached externally on said films to the outer surface of said proximal and distal side walls, respectively, of said drainage portion, the pouch further comprising a flap of flexible material having an edge portion attached to one of said side walls in spaced relation to said proximal and distal stiffening strips, said flap of flexible material having a first securing strip of an interlocking means attached on an unsecured portion of said flap that can be rotated relative to said one of said side walls about an angle formed between said edge portion and the remainder of said flap, and a second securing strip of a corresponding interlocking means attached to the other of said side walls intermediate said proximal and distal stiffening strips and said flap of flexible material for securing a coil comprised of: i) each of said proximal and distal stiffening strips rotated upwards at least two times and ii) said coil fitting snuggly and tightly in said angle formed between said edge portion and the remainder of said flap with said interlocking means of said first and second securing strips in engagement, wherein the second securing strip is longitudinally spaced away from the proximal stiffening strip with a distance of at least a longitudinal width of the distal stiffening strip, such that the distal stiffening strip abuts an area of the distal side wall between distal stiffening strip and the second securing strip after the proximal and distal stiffening strips are rotated upwards once, wherein the first and second securing strips are the only means for securing the coil.

2. A pouch according to claim 1, wherein said edge portion of said flap of flexible material is attached to one of said side walls in a substantially parallel relationship with said drainage opening by means of an attachment zone, said proximal and distal stiffening strips and said first and second securing strips also being attached to the respective ones of said side walls in a substantially parallel relationship with said drainage opening.

3. A pouch according to claim 2, wherein a gripping tab for being gripped by fingers of a hand projects from said flap of flexible material.

4. A pouch according to claim 2 or 3, wherein said angle formed between said edge portion and the remainder of said flap is spaced from said drainage opening by a distance substantially equal to a multiple of the width of the widest of said proximal and distal stiffening strips.

5. A pouch according to claim 1 and further provided with a film arranged between said films forming said proximal and distal side walls for dividing said cavity into two compartments and ending at a transversely extending bottom edge located between said films to which said proximal and distal stiffening strips are attached and spaced from said drainage opening.

6. A pouch according to claim 5, wherein said film dividing said cavity into two compartments is provided at or near its upper end with an opening for the passage of flatus gasses between said compartments.

7. A pouch according to claim 1, wherein the films forming said two side walls of the drainage portion are attached to each other along longitudinal edges thereof by means of edge seams of at least one of heat sealing or adhesive, and at least one of said stiffening strips has an extension extending beyond one of said edge seams.

8. A pouch according to claim 7, wherein the proximal stiffening strip is configured such that at least one of two opposed end portions thereof slopes in a distal direction thereof.

9. A pouch according to claim 1, wherein a gripping tab of flexible sheet material is attached to the outer surface of at least one of the proximal or distal side wall or proximal or distal stiffening strip in a region near said drainage opening.

10. A pouch according to claim 1, including a further stiffening strip disposed between the corresponding one of said proximal and distal stiffening strips and said second securing strip for forming a coil comprised of said proximal and distal stiffening strips, said further stiffening strip and said second securing strip.

* * * * *

UNITED STATES PATENT AND TRADEMARK OFFICE
CERTIFICATE OF CORRECTION

PATENT NO. : 9,629,744 B2  
APPLICATION NO. : 12/973073  
DATED : April 25, 2017  
INVENTOR(S) : Tine Villefrance et al.

It is certified that error appears in the above-identified patent and that said Letters Patent is hereby corrected as shown below:

On the Title Page

In the Second Page, Item (56), Other Publication, Column 2, Line 1, "tor" to read as --for--.

In the Specification

Column 3, Line 27, "may by" to read as --may be--.

Signed and Sealed this  
Twenty-fifth Day of July, 2017

Joseph Matal  
*Performing the Functions and Duties of the*  
*Under Secretary of Commerce for Intellectual Property and*  
*Director of the United States Patent and Trademark Office*